US008703764B2

(12) United States Patent
Sheldon

(10) Patent No.: US 8,703,764 B2
(45) Date of Patent: Apr. 22, 2014

(54) COMBINATION THERAPY FOR DEMENTIA, DEPRESSION AND APATHY

(76) Inventor: Leslie James Sheldon, Burnaby (CA)

(*) Notice: Subject to any disclaimer, the term of this patent is extended or adjusted under 35 U.S.C. 154(b) by 687 days.

(21) Appl. No.: 11/437,409

(22) Filed: May 19, 2006

(65) Prior Publication Data

US 2006/0287299 A1 Dec. 21, 2006

Related U.S. Application Data

(63) Continuation of application No. PCT/CA2004/002071, filed on Dec. 2, 2004.

(60) Provisional application No. 60/526,137, filed on Dec. 2, 2003.

(51) Int. Cl.
| A61K 31/551 | (2006.01) |
| A61K 31/497 | (2006.01) |
| A61K 31/519 | (2006.01) |
| A61K 31/445 | (2006.01) |
| A61K 31/34 | (2006.01) |
| A61K 31/135 | (2006.01) |

(52) U.S. Cl.
USPC . 514/220; 514/253.07; 514/317; 514/259.41; 514/649; 514/419; 514/469

(58) Field of Classification Search
None
See application file for complete search history.

(56) References Cited

U.S. PATENT DOCUMENTS

| 5,648,396 A | 7/1997 | Young et al. | |
| 6,555,585 B2 * | 4/2003 | Shirvan et al. | 514/616 |
| 2002/0151543 A1 | 10/2002 | Barberich et al. | |
| 2002/0193429 A1 | 12/2002 | Tsai et al. | |
| 2003/0032636 A1 | 2/2003 | Cremers et al. | |
| 2003/0212060 A1 | 11/2003 | Tollefson | |
| 2004/0204401 A1 * | 10/2004 | Migaly | 514/220 |

FOREIGN PATENT DOCUMENTS

| EP | 0830864 | | 3/1998 | |
| EP | 0958824 | | 11/1999 | |
| EP | 1016664 | A1 | 7/2000 | |
| WO | 9959593 | | 11/1999 | |
| WO | WO 99/61027 | * | 12/1999 | A61K 31/55 |
| WO | WO9962522 | A1 | 12/1999 | |
| WO | WO0006140 | A2 | 2/2000 | |
| WO | WO03066039 | A1 | 8/2003 | |

OTHER PUBLICATIONS

Marin, R. S. Am. J. Psychiatry 147:1, Jan. 1990; p. 22-30.*
The Merck Manual of Diagnosis and Therapy, Seventeenth Edition, published 1999 by Merck Research Laboratories, ed. by Beers and Berkow, pp. 1531-1538 and 1569-1570.*
Sajatovic et al. J. Clin. Psychiatry 62:9, Sep. 2001; p. 728-732.*
Jordan, V. C. Nature Reviews: Drug Discovery, 2, 2003, p. 205-213.*
Padala et al. Treatment of Apathy with Methylphenidate. J. Neuropsychiatry Clin. Neurosci., 2007,19(1); pp. 81-83.*
Van Reekum et al (J. Neuropsychiatry Clin. Neurosci., 2005, 17(1); p. 7-19.*
Entsuah et al. (J. Clin. Psychiatry 2001; 62: 869-877; abstract).*
Marin et al. (J. Nerv. Ment. Dis. 182(4); p. 235-239, (1994).*
CA 02364211 A1.*
Marin, R. S. (Am. J. Psychiatry 147:1, Jan. 1990).*
Marangell et al. (J. Clin. Psychiatry 63: 5, May 2002; p. 391-395).*
Kenneth Bender (Psychiatric Times, Aug. 1, 1999).*
Robert S. Marin (Seminars in Clinical Neuropsychiatry, vol. 1, No. 4 (Oct. 1996): pp. 304-314.*
Mann, R.S. "Apathy: concept, syndrome, neural mechanisms, and treatment", Semin clin Neuropsychiatry, 1996, 1(4):304-314.
V. Chan-Palay "Depression and Senile Dementia of the Alzheimer Type: A Role for Moclobemide," Psychopharmacology (1992) 106:S137-S139.
Amrein et al, "Moclobemide in Patients with Dementia and Depression," Parkinson's Disease: Advance in Neurology (1999) 80:509-519.
Wasbes et al. "Potential of Moclobemide to Improve Cerebral Insufficiency Identified Using a Scopolamine Model of Aging and Dementia," Acta Psychiatr Scand (1990) 360:71-72.
Tolbert et al. "Selegiline in Treatment of Behavariol and Cognitive Symptoms of Alzheimer Disease," The Annals of Pharmacotherapy (1996) 30:1122-1129.
Tariot et al. "Pharmacologic Therapy for Behavioral Symptoms of Alzheimer's Disease," Clinics in Geriatric Medicine (2001) 17(2):3599-376.
Gareri et al. "Conventional and Atypical Antipsychotics in the Elderly," http://www.medscape.com/viewarticle/457366 Feb. 28, 2005.
Schatz "Olanzapine for Psychotic and Behavioral Disturbances in Alzheimer Disease," The Annals of Pharmacotherapy (2003) 37:1321-1324.
De Deyn et al. "A Randomized Trial of Risperidone, Placebo, and Haloperidol for Behavioral Symptoms of Dementia," Neurology (1999) 53:946-955.
Katz et al. "Comparison of Risperidone and Placebo for Psychosis and Behavioral Disturbances Associated with Dementia: A Randomized, Double-Blind Trial," J. Clin Psychiatry (1999) 60:107-115.
Breitbart, W et al., "Neuropsychiatric Syndromes and Psychological Symptoms in Patients with Advanced Cancer" Journal of Pain and Symptom Management vol. 10, No. 2 (1995) pp. 131-141.

(Continued)

*Primary Examiner* — Noble Jarrell
*Assistant Examiner* — Valerie Rodriguez-Garcia
(74) *Attorney, Agent, or Firm* — Bozicevic, Field & Francis LLP; Bret E. Field; Khin K. Chin

(57) ABSTRACT

The invention provides, in part, methods and compositions for treating psychiatric disorders, for example, apathy, dementia, or depression, using combination therapies such a monoamine oxidase inhibitor or a selective serotonin reuptake inhibitor in combination with an anti-psychotic agent.

15 Claims, No Drawings

(56) References Cited

OTHER PUBLICATIONS

Glenn, M.B., et al. "Cutoff score on the apathy evaluation scale in subjects with traumatic brain injury", Brain Inj, 2002, 16(6): 509-516.

Kuzis, G. et al. "Neuropsychological correlates of apathy and depression in patients with dementia", Neurology, 1999, 52(7):1403-7.

Marin, R.S. "Apathy: concept, syndrome, neural mechanisms, and treatment", Semin clin Neuropsychiatry, 1996, 1(4):304-314.

Marin, R. S., et al. "Group differences in the relationship between apathy and depression", Journal of Nervous Mental Disorders, 1994, 182(4):235-9.

Robert, P.H., et al. "The apathy inventory: assessment of apathy and awareness in Alzheimer's disease, Parkinson's disease and mild cognitive impairment", Int J Geriatr Psychiatry, 2002, 17(2):1099-105.

Adler et al., "Pharmacological treatment of frontotemporal dementia: treatment response to the MAO-A inhibitor moclobemide" J. of Geriatric Psychiatry, vol. 18, No. 7, pp. 653-655 (2003).

Pollak P., Rev Neurol (Paris). Abstract Only 2002 158 1:S125-31.

\* cited by examiner

COMBINATION THERAPY FOR DEMENTIA, DEPRESSION AND APATHY

CROSS-REFERENCE

This application is a continuation of PCT Application No. PCT/CA2004/002071, filed Dec. 2, 2004, which claims benefit of U.S. Provisional Patent Application No. 60/526,137, filed Dec. 2, 2003, both of which are incorporated herein by reference in their entirety noting that the current application controls to the extent there is any contradiction with any earlier applications and to which applications we claim priority under 35 USC §120 and 119

FIELD OF THE INVENTION

The invention is in the field of pharmaceutical therapies for psychiatric disorders such as apathy, dementia, or depression.

BACKGROUND OF THE INVENTION

With increasing awareness of mental health issues and knowledge of the nervous system and neuropharmacology, progress has been made in the treatment of common psychiatric disorders, including dementia, depression, and apathy. There is however still a need for effective therapies that can stop, slow, reverse, or prevent the indications of dementia, depression, and apathy that accompany diverse mental disorders. There is also a need to refine and further characterise the diagnostic criteria that may be used to differentiate patients amenable to alternative therapeutic regimens.

SUMMARY OF INVENTION

The invention provides, in general, methods and compositions for treating psychiatric disorders, for example, apathy, dementia, or depression, using combination therapies such as a monoamine oxidase inhibitor or a selective serotonin reuptake inhibitor, in combination with an anti-psychotic agent.

In one aspect of the invention, there is provided, a method of treating dementia, depression, or apathy in a human subject, by administering a pharmaceutically effective amount of a monoamine oxidase inhibitor or a selective serotonin reuptake inhibitor, in combination with an anti-psychotic agent to the subject. The subject may for example have been diagnosed as being in need of such treatment in accordance with generally accepted clinical criteria, or criteria as disclosed herein.

In an alternative aspect of the invention, there is provided the use of a pharmaceutically effective amount of a monoamine oxidase inhibitor or a selective serotonin reuptake inhibitor in combination with an anti-psychotic agent for the preparation of a medicament for treating dementia, depression, or apathy.

In an alternative aspect of the invention, there is provided a pharmaceutical composition for treating dementia, depression, or apathy, including a monoamine oxidase inhibitor or a selective serotonin reuptake inhibitor in combination with an anti-psychotic agent. The pharmaceutical composition may also comprise a pharmaceutically acceptable carrier.

In an alternative aspect of the invention, there is provided a kit for treating dementia, depression, or apathy, including a monoamine oxidase inhibitor or a selective serotonin reuptake inhibitor in combination with an anti-psychotic agent.

In alternative embodiments, the monoamine oxidase inhibitor may be a reversible monoamine oxidase inhibitor, for example, a reversible monoamine oxidase-A inhibitor, such as moclobemide, brofaromine, befloxatone, or toloxatone; the selective serotonin reuptake inhibitor may be fluoxetine, citalopram, fluvoxamine, sertraline, or paroxetine; and the anti-psychotic agent may for example be an atypical anti-psychotic agent, for example, risperidone, olanzapine, zotepine, ziprasidone, quetiapine, sertindole, or clozapine. The monoamine oxidase inhibitor may for example be selected from the group: isocarboxazid; pargyline; selegiline; furazolidone; phenelzine; amiflamine; iproniazid; nialamide; tranylcypromine; octamoxin; phenoxypropazine; pivalyl benzhydrazine; iproclozide; iproniazide; bifemelane; prodipine; benmoxin; etryptamine; fenoxypropazine; mebanazine; pheniprazine; safrazine; hypericine; iproniazid phosphate; phenelzine sulphate; tranylcypromine sulphate; moclobemide; brofaromine; befloxatone; toloxatone; clorgyline; L 51. 641; L 54. 761; L 54. 832; LY 121. 768; cimoxatone; bazinaprine; BW-1370U87; E-2011; harmine; harmaline; RS-8359; T-794; MDL 72394; MDL 72392; sercloremine; esuprone; clorgyline hydrochloride; mixtures thereof; and pharmaceutically acceptable salts thereof. The selective serotonin reuptake inhibitor may for example be selected from the group: fluoxetine; citalopram; fluvoxamine; sertraline; paroxetine; escitalopram; femoxetine; ifoxetine; indeloxazine; binedaline; nefazodone; trazodone; etoperidone; milnacipran; venlafaxine; desvenlafaxine; citalopram hydrobromide; fluoxetine hydrochloride; fluvoxamine maleate; paroxetine hydrochloride; sertraline hydrochloride; mixtures thereof; and pharmaceutically acceptable salts thereof. The combination may be synergistically effective at reducing any of the indications of dementia, depression, or apathy.

The composition may include moclobemide at a daily dosage of about 150 mg to about 600 mg, and any one of risperidone at a daily dosage of about 0.625 mg to about 3 mg, olanzapine at a daily dosage of about 0.625 mg to about 10 mg, zotepine at a daily dosage of about 12.5 mg to about 300 mg, ziprasidone at a daily dosage of about 1.00 mg to about 80 mg, quetiapine at a daily dosage of about 12.5 mg to about 800 mg, sertindole at a daily dosage of about 6.25 mg to about 450 mg or clozapine at a daily dosage of about 1.00 mg to about 900 mg, per day, respectively. Alternatively the composition may include venlafaxine at a daily dosage of about 37.5 mg to about 375 mg, and any one of risperidone at a daily dosage of about 0.625 mg to about 3 mg, olanzapine at a daily dosage of about 0.625 mg to about 10 mg, zotepine at a daily dosage of about 12.5 mg to about 300 mg, ziprasidone at a daily dosage of about 1.00 mg to about 80 mg, quetiapine at a daily dosage of about 12.5 mg to about 800 mg, sertindole at a daily dosage of about 6.25 mg to about 450 mg or clozapine at a daily dosage of about 1.00 mg to about 900 mg, per day, respectively.

A "pharmaceutically effective amount" refers to an amount effective, at dosages and for periods of time necessary, to achieve a desired therapeutic or prophylactic result, such as reduction of any of the indications of dementia, depression, or apathy. A pharmaceutically effective amount of a combination of a monoamine oxidase inhibitor or a selective serotonin reuptake inhibitor and an anti-psychotic agent, according to the invention, may vary according to factors such as the disease state, age, sex, and weight of the individual, and the ability of the combination to elicit a desired response in the individual. Dosage regimens may be adjusted to provide the optimum therapeutic or prophylactic response. A pharmaceutically effective amount is also generally one in which any toxic or detrimental effects of the combination are outweighed by the therapeutically or prophylactically beneficial effects, although an assessment of benefit or detriment may vary according to the severity of the condition to be treated.

A "synergistically effective" combination of a monoamine oxidase inhibitor or a selective serotonin reuptake inhibitor with an anti-psychotic agent is characterised by the fact that the monoamine oxidase inhibitor or the selective serotonin reuptake inhibitor is administered in a pharmaceutically effective amount and the anti-psychotic agent is administered in a pharmaceutically effective amount also, and the therapeutic effect thereby achieved, such as a reduction of any of the indications of dementia, depression, or apathy, is greater than the sum of the therapeutic effect that would be achieved with the monoamine oxidase inhibitor or the selective serotonin reuptake inhibitor alone in the pharmaceutically effective amount plus the therapeutic effect that would be achieved with the anti-psychotic agent alone in the pharmaceutically effective amount. For example, a synergistically effective combination of risperidone and moclobemide is a combination wherein the moclobemide is administered in a pharmaceutically effective amount and risperidone is administered in a pharmaceutically effective amount, and the therapeutic effect on the indications of dementia, depression, or apathy thereby achieved is greater than the sum of the inhibition that would be achieved with risperidone alone in the pharmaceutically effective amount plus the inhibition that would be achieved with moclobemide alone in the pharmaceutically effective amount. Similarly, a synergistically effective combination of olanzapine and venlafaxine is a combination wherein the venlafaxine is administered in a pharmaceutically effective amount and olanzapine is administered in a pharmaceutically effective amount, and the therapeutic effect on the indications of dementia, depression, or apathy thereby achieved is greater than the sum of the inhibition that would be achieved with olanzapine alone in the pharmaceutically effective amount plus the inhibition that would be achieved with venlafaxine alone in the pharmaceutically effective amount.

"Treating", "treatment" or "to treat" as used herein means the medical management of a subject, usually a human subject, with the intent that a cure, amelioration, or prevention of dementia, depression, or apathy will result. This term includes active treatment, that is, treatment directed specifically toward improvement of dementia, depression, or apathy, and also includes causal treatment, that is, treatment directed toward removal of dementia, depression, or apathy. In addition, this term includes palliative treatment, that is, treatment designed for the relief of symptoms rather than the curing of dementia, depression, or apathy; preventive treatment, that is, treatment directed to prevention of dementia, depression, or apathy; and supportive treatment, that is, treatment employed to supplement another specific therapy directed toward the improvement of dementia, depression, or apathy.

DETAILED DESCRIPTION OF THE INVENTION

In general, the invention provides methods and compositions for treating dementia, depression, or apathy associated with diverse mental disorders. The compositions of the invention include a monoamine oxidase inhibitor (MAOI) or a selective serotonin reuptake inhibitor (SSRI) in combination with an anti-psychotic agent.

Treatment of dementia, depression, or apathy using the combination compositions of the invention is more effective, in some embodiments, than that achieved in the absence of treatment (i.e., without employing exogenous agents or therapeutics) or by treatment with a MAOI or SSRI alone, or an anti-psychotic agent alone, wherein the combination is administered in a "synergistically effective" amount. In some embodiments, the combination compositions of the invention are useful in treating forms of dementia, depression, or apathy that are refractory to treatment using other therapeutic approaches.

In some embodiments, certain combinations are excluded from use according to aspects of the invention. For example, in some embodiments, a SSRI in combination with an anti-psychotic agent may be excluded as a therapy or prophylaxis, according to the invention, for any one or more of the disorders of dementia, depression, or apathy. In other embodiments, a MAOI or a reversible inhibitor of monoamine oxidase A (RIMA), in combination with an antagonist or agonist of a 5-HT receptor, or an anti-psychotic agent, may be excluded, for example, for the treatment of depression. In other embodiments, a combination of phenelzine and zisperidone may be excluded for the treatment of depression. In other embodiments, a combination of moclobemide with an atypical anti-psychotic agent may be excluded from the treatment of depression.

Dementia

Dementia is a neurodegenerative disorder generally characterized as the loss of an individual's learning and cognitive abilities, and is usually accompanied by behavioral, psychological, and motor symptoms. A critical element of dementia is the deficiency in short- and long-term memory, associated with difficulties in abstract thought, faulty judgment, personality change, and other impairments of higher cortical function. These impairments are generally so severe that the patient cannot maintain normal social activities or relationships. Typically, the loss of cognitive skills and memory in dementia is slow, with mental deterioration taking place over years. Dementia is most common among the elderly, and is becoming more widespread as the populations of developing countries age.

Many different dementias have been enumerated. For example, cortical dementia, fronto-temporal dementia, Alzheimer's dementia, lewy body dementia, progressive dementia, vascular dementia, multi-infarct dementia, drug- or alcohol-related dementia, and Parkinson's-related dementia. Dementia may also result from head injury, cardiac arrest, radiation therapy for cancer, Acquired Immunodeficiency Syndrome (AIDS), Pick's disease, or Creutzfeldt-Jakob disease, including its variant form. Dementia is usually diagnosed according to its etiology, the two most common etiologies being Alzheimer's dementia and vascular dementia, for example, following stroke, in the elderly. Dementia is usually progressive and irreversible unless the etiology itself is treatable. Many patients have more than one type of dementia. A diagnosis of dementia generally involves ruling out major depressive disorder or delirium.

In most dementias, patients often exhibit primary cognitive symptoms as well as secondary behavioral symptoms. Cognitive symptoms may include things such as loss of memory, orientation perception, language and impaired judgement. Secondary or behavioral symptoms may include such things as personality and behavioral changes where the patient is aggressive or verbally agitated. Patients with dementia are often treated with anti-psychotic agents, benzodiazepines, beta-blockers, SSRIs, anti-depressants, anti-convulsives, and dietary supplements with limited efficacy.

Depression

Depression or depressive disorders generally manifest as feelings of intense sadness and despair that are not attributable to other causes, such as bereavement. Depressed patients may experience mental slowness and a loss of concentration, insomnia or hypersomnia, anorexia or weight gain, decreased energy and libido and disruption of normal circadian rhythms, body temperature and endocrine functions. The most common types of depression include unipolar or major depression, dysthymia, and bipolar disorder, which differ in the number of symptoms, severity, and persistence.

"Unipolar depression" or "major depression" generally means a clinical course where an individual experiences a period of at least two weeks during which there is either depressed or irritable mood or a marked loss of interest or pleasure in almost all activities. In children and adolescents, the mood may more generally be irritable rather than sad. The individual also experiences at least four additional symptoms drawn from a list that includes significant changes in appetite or weight (e.g., a change of more than 5% of body weight in a month), sleep, and psychomotor activity; fatigue or loss of energy; feelings of worthlessness or inappropriate guilt (which may be delusional); difficulty thinking, concentrating, or making decisions; or recurrent thoughts of death or suicidal ideation, plans, or attempts. Each symptom must be newly present or must have clearly worsened compared with the person's pre-episode status. The symptoms must persist for most of the day, nearly every day, for at least two consecutive weeks, and the episode must be accompanied by clinically significant distress or impairment in social, occupational (or academic), or other important areas of functioning. The episode may be a single episode or may be recurrent.

Major depression is thus characterized by one or more major depressive episodes in an individual without a history of manic, mixed, or hypomanic episodes. The diagnosis of unipolar or major depression is not made if: manic, mixed, or hypomanic episodes develop during the course of depression; if the depression is due to the direct physiological effects of a substance; if the depression is due to the direct physiological effects of a general medical condition; if the depression is due to a bereavement or other significant loss ("reactive depression"); or if the episodes are better accounted for by schizoaffective disorder and are not superimposed on schizophrenia, schizophreniform disorder, delusional disorder, or psychotic disorder. If manic, mixed, or hypomanic episodes develop, then the diagnosis is changed to a bipolar disorder.

"Dysthymia" is a less severe form of depression that involves a chronic malaise and exhibits many of the symptoms of major depression, but is not as disabling as is major depression. Dysthymia prevents an individual from functioning at his or her optimum level and is a long-term, low-grade disorder. An individual with dysthymia is likely to have at least one major depressive episode at some point. Thus, "dysthymia" or "dysthymic disorder" generally means a chronically depressed mood that occurs for most of the day, more days than not, for at least two years. In children and adolescents, the mood may be irritable rather than depressed, and the required minimum duration is one year. During the two year period (one year for children or adolescents), any symptom-free intervals last no longer than 2 months. During periods of depressed mood, at least two of the following additional symptoms are present: poor appetite or overeating, insomnia or hypersomnia, low energy or fatigue, low self-esteem, poor concentration or difficulty making decisions, and feelings of hopelessness. The symptoms may cause clinically significant distress or impairment in social, occupational (or academic), or other important areas of functioning. The diagnosis of dysthymia is not made if: the individual has ever had a manic episode, a mixed episode, a hypomanic episode; has ever met the criteria for a cyclothymic disorder; the depressive symptoms occur exclusively during the course of a chronic psychotic disorder (e.g., schizophrenia); or if the disturbance is due to the direct physiological effects of a substance or a general medical condition. After the initial two-years of dysthymic disorder, major depressive episodes may be superimposed on the dysthymic disorder ("double depression").

"Bipolar disorder," also known as manic-depression, is characterized by severe mood swings, from high (mania) to low (depression). The mood swings may be abrupt or gradual. During the lows, an individual with bipolar disorder generally exhibits one or more of the symptoms of a depressive disorder.

Depression is often co-morbid with chronic general medical conditions, for example, cancer, diabetes, heart disease, stroke, HIV/AIDS, Parkinson's disease, particularly in the elderly. Empirically, women are more likely to suffer from a form of depression than men. In addition to psychotherapy and electroconvulsive therapy, patients with a form of depression are often treated with tricyclic anti-depressants (TCAs), MAOIs, SSRIs, and psychotropic drugs.

Apathy

Apathy is generally a behavioral disorder that is related to, but can be differentiated from, depression. Apathy is often defined as a lack of motivation not attributable to cognitive impairment, emotional distress, or decreased consciousness. Patients with apathy often have slowness of thinking and a decrease in their ability to refocus their thinking to accommodate a new topic. In addition, apathy is not a general decrease in cognitive function, but is rather associated with specific areas of cognitive dysfunction (Andersson S and A M Bergedalen, J Nerv Ment Dis 182:235-9, 1994; Kuzis et al. Neurology 52:1403-7, 1999).

Apathy refers to a syndrome closely related to major depression in that apathy is characterized by a lack of feeling or emotion or indifference. However, Apathy may be distinguished from major depression by the absence of depressed mood.

Apathy may also be of two types:
1. The inability to generate the feelings; and
2. The inability to motivate the self to experience the feelings.

Apathy may manifest during the course of unrelated neuropsychiatric disorders such as schizophrenia, Parkinson's Disease, Alzheimer's Disease, Multiple Sclerosis, Huntington's Disease, HIV/AIDS, stroke, head injury, myotonic dystrophy, cerebrovascular lesions, and frontal lobe lesions. Diagnosing apathy in a patient requires that abulia, akinesia, akinetic mutism, depression, dementia, delirium, despair, and demoralization first be ruled out.

Individuals diagnosed with apathy have been treated with agents such as methylphenidate, pemoline, dextroamphetamine, amantadine, amphetamine, bromocriptine, bupropion, or selegiline.

Diagnosis

The Diagnostic and Statistical Manual of Mental Disorders IV-TR, Fourth Edition, Text Revision, Wash., American Psychiatric Association, 2000 ("DSM-IV-TR") is commonly used among practitioners for diagnosing and treating mental disorders. An alternative standard for diagnosing mental disorders is provided by the tenth revision of the International Statistical Classification of Diseases and Related Health Problems ("ICD-10") under the aegis of the WHO. The ICD criteria are perhaps more prevalent in Europe than in North America, although the DSM-IV-TR is used extensively internationally. The National Institute for Neurological Disorders and Stroke-Association Internationale pour la Recherche et l'Enseignement en Neurosciences (NINDS-AIREN) also maintains a standard for diagnosis of mental disorders. With respect to the diagnosis of apathy, various measures are used, including the Apathy Inventory (Robert, P H et al., 2002, Int J Geriatr Psychiatry 17:1099-105), the Apathy Evaluation Scale (Marin, R S, 1996, Seminars Clin Neuropsychiatry; 1: 304-314), and the Apathy Scale of Glenn et al. (Glenn M B et al., 2002, Brain Injury 16: 509-516). Diagnoses of dementia, depression, or apathy according to the invention may be performed using criteria established by the DSM-IV-TR, ICD-10, NINDS-AIREN, the different apathy scales, or any other standard accepted by mental health practitioners. Diagnoses of dementia, depression, or apathy according to the invention may also be performed using newly established or experimental criteria.

In some embodiments for diagnosis of a subject in need of treatment in accordance with the invention, Apathy may be defined as a syndrome closely related to major depression in that apathy is characterized by a lack of feeling or emotion, or indifference. However, Apathy may be distinguished from major depression by the absence of depressed mood.

In some embodiments Apathy may also be considered as being of two types:
1. The inability to generate the feelings; and
2. The inability to motivate the self to experience the feelings.

Monoamine Oxidase Inhibitors

Monoamine oxidase inhibitors or MAOIs are a chemically heterogeneous class of anti-depressants that inhibit or affect the activity of monoamine oxidase in the brain, slowing the breakdown of monoamine neurotransmitters, thus affecting mood. Some non-selective MAO inhibitors have severe side effects, including adverse food and drug interactions. Some example of MAOIs include, but are not limited to the following:
  isocarboxazid (Marplan® (Oxford Pharm.); CAS #59-63-2);
  pargyline (N-Methyl-N-propargylbenzylamine; CAS #555-57-7);
  selegiline (Elderpryl® (Somerset); CAS #14611-51-9);
  furazolidone (CAS #67-45-8);
  phenelzine (Nardil® (Pfizer); CAS #51-71-8);
  amiflamine ((+/−)-4-dimethylamino-a, 2-dimethylphenethylamine; Astra; CAS #77518-07-1);
  iproniazid (isonicotinic acid-2-isopropylhydrazide; CAS #54-92-2);
  nialamide (N-[2-(benzylcarbamoyl)ethyl]-N'-isonicotinyl hydrazide; CAS #51-12-7);
  tranylcypromine (Parnate® (GlaxoSmithKline); CAS #155-09-9);
  octamoxin (1-methylheptyl-hydrazine; CAS #4687-87-1);
  phenoxypropazine (Drazine®);
  pivalyl benzhydrazine;
  iproclozide (N'-(p-chlorophenoxyacetyl)-N'-isopropylhydrazine; CAS #3544-35-2);
  iproniazide (N-isonicotinyl-N'-isopropylhydrazine; CAS #54-92-2);
  bifemelane (4-(o-benzylphenoxy)-N-methylbutylamine (hydrochloride); CAS #90293-01-9);
  prodipine (1-(1-methylethyl)-4,4-diphenylpiperidine or 1-isopropyl-4,4-diphenylpiperidine; CAS #31314-38-2);
  benmoxin (N'-(a-methylbenzyl)benzohydrazine; CAS #7654-03-7);
  etryptamine (a-ethyl-1H-indole-ethanamine; CAS #2235-90-7);
  fenoxypropazine (1-methyl-2-phenoxyethyl)hydrazine; CAS #3818-37-9);
  mebanazine (CAS #65-64-5);
  pheniprazine (a-methylphenethyl-hydrazine (hydrochloride); CAS #55-52-7);
  safrazine (1-methyl-3-(3,4-methylenedioxyphenyl) propylhydrazine);
  hypericine (1,3,4,6,8,13-hexahydro-10.11-dimethylphenathro[1, 10.9, 8]perylen-7,14-dione; CAS #548-04-9); and
  pharmaceutically acceptable salts thereof (for example iproniazid phosphate CAS #305-33-9; phenelzine sulphate CAS #156-51-4; and tranylcypromine sulphate CAS #13492-01-8).

Selective MAO A inhibitors include, but are not limited to the following:
  moclobemide (CAS #71320-77-9);
  brofaromine (CAS #63638-91-5);
  befloxatone (CAS #134564-82-2);
  toloxatone (CAS #29218-27-7);
  clorgyline (N-methyl-N-propargyl-3-(2,4-dichlorophenoxy) propylamine; CAS #17780-72-2);
  L 51. 641 (Lilly) N-[2-(o-chlorophenoxy)ethyl]cyclopropylamine;
  L 54. 761 (Lilly) phenacyl-cyclopropylamine;
  L 54. 832 (Lilly) 2-naphthoylmethyl-cyclopropylamine;
  LY 121. 768 (Lilly) N-[2-(o-iodophenoxy)ethyl]cyclopropylamine;
  cimoxatone (3-[4-(5-methoxymethyl-2-oxo-oxazolidin-3-yl) phenoxymethyl]benzonitrile; CAS #73815-11-9);
  bazinaprine (3-[2-(morpholinoethyl)amino]-6-phenylpyridazine-4-carbonitrile; CAS #94011-82-2);
  BW-1370U87 (Burroughs Wellcome—1-ethylphenoxathiin-10,10-dioxide);
  E-2011 (Eisai—(5R)-3-[2-((1S)-3-cyano-1hydroxypropyl)benzothiazol-6-yl]-5-methoxymethyl-2-oxazolidine);
  harmine (7-methoxy-1-methyl-β-carboline; CAS #442-51-3);
  harmaline (3,4-dihydro-7-methoxy-1-methyl-β-carboline; CAS #304-21-2);
  RS-8359 (Sankyo—(+/−)-4-(4-cyanoanilino)-5,6-dihydro-7-hydroxy-7H-cyclopenta[d]-pyrimidine);
  T-794 (Tanabe Seiyaku—[(5R)-3-(6-(cyclopropylmethoxy) 2-naphthalenyl)-5-(methoxymethyl) 2-oxazolidone]);
  MDL 72394 (Marion Merrell—(E)-beta-Fluoromethylene-m-tyrosine);
  MDL 72392 (Marion Merrell—(E)-beta-fluoromethylene-m-tyramine);
  sercloremine (4-(5-chloro-2-benzofuranyl)-1-methylpiperidine (hydrochloride) Novartis—Ciba-Geigy);
  esuprone (3,4-dimethyl-2-oxo-2H-1-benzopyran-7-yl ethanesulfonate or 7-hydroxy-3,4-dimethylcoumarin ethanesulfonate; (Knoll) CAS #91406-11-0); and
  pharmaceutically acceptable salts thereof (for example clorgyline hydrochloride CAS #17780-75-5).

Some of the selective MAO A inhibitors listed above may have mixed MAO A and MAO B inhibitory activity, may be a bioprecursor which liberates an MAO A inhibitor when administered and may also be reversible MAO inhibitor.

Reversible inhibitors of monoamine oxidase Type A (RIMAs) are a sub-class of MAOIs that preferentially inhibit isoenzyme A of monamine oxidase and are reversible. RIMAs are considered safer and substantially more free of side effects, perhaps because isoenzyme B remains available to metabolize tyramine, which is present in some foods. RIMA anti-depressants include, but are not limited to, moclobemide, brofaromine, befloxatone (Bristol-Myers Squibb; (R)-5-(methoxymethyl)-3-(p[(R)-4,4,4-trifluoro-3-hydroxybutoxy]phenyl]-2-oxazolidinone; CAS #134564-82-2) and toloxatone.

Moclobemide (Manerix® (Roche); p-chloro-N-(2-morpholinoethyl) benzamide; CAS #71320-77-9) is an anti-depressant that affects the monoaminergic cerebral neurotransmitter system in a reversible manner. As a result of moclobemide treatment, patients generally have decreased metabolism of dopamine, norephinephrine and serotonin, therefore increasing the extracellular concentrations of these neurotransmitters. Moclobemide is often prescribed for major depression or in extreme cases of social phobia. U.S. Pat. No. 4,210,754 issued to Berkhard et al. (Jul. 1, 1980), describes the compound moclobemide along with other related benzamides. Moclobemide's use in depression appears to have similar efficacy as that of TCAs, SSRIs, and non-selective irreversible MAOIs. However, moclobemide seems to have much fewer side effects than other anti-depressant treatments, as well as fewer food and drug interactions. For these reasons, moclobemide has been widely used as an anti-depressant. Brofaromine (Consonar® (Novartis—Ciba-Geigy); 4-(5-methoxy-2 benzofuranyl)-piperidine; CAS #63638-91-5) described in U.S. Pat. No. 4,210,655, and toloxatone (5-(hydroxymethyl)-3-m-tolyl-2-oxazolidinone; CAS #29218-27-7), are RIMAs that are reported to have decreased extra-pyramidal effects, similar to moclobemide.

Selective Serotonin Reuptake Inhibitors

Selective serotonin reuptake inhibitors or SSRIs are antidepressant agents that increase the levels of serotonin (5-hydroxytryptamine or 5-HT) in the body by blocking the presynaptic serotonin transporter receptor. In some cases, SSRIs also affect the norepinephrine and/or the dopamine transporters, although to a lesser extent. Although SSRIs can have some side effects, including adverse food and drug interactions, in general they are considered more safe than older antidepressants and have been prescribed extensively. While SSRIs have been primarily prescribed for anxiety disorders and unipolar and bipolar major depression, their use in the treatment of other psychiatric conditions such as dysthymia, premenstrual syndrome, bulimia nervosa, obesity, obsessive compulsive disorder, borderline personality disorder, alcoholism, rheumatic pain, and migraine headache has been supported. Examples of SSRIs include, but are not limited to the following:

fluoxetine (Prozac®) (3-[(p-trifluoromethyl)phenoxy]-N-methyl-3-phenylpropylamine (hydrochloride); CAS #54910-89-3);

citalopram (Celexa®) (1-[3-(dimethylamino)propyl]-1-(p-fluorophenyl)-1,3-dihydro-isobenzofuran-5-carbonitrile; CAS #59729-33-8);

fluvoxamine (Luvox®) ((E)-5-methoxy-4'-(trifluoromethyl)valerophenone O-(2-amino-ethyl)oxime (hydrogen maleate); CAS #54739-18-3);

sertraline (Zoloft®) ((+)-cis(1S,4S)-4-(3,4-dichlorophenyl)-1,2,3,4-tetrahydro-N-methyl-1-naphthylamine (HCl); CAS #79617-96-2);

paroxetine (Paxil®) ((3S-trans)-3-[(1,3-benzodioxol-5-yloxy) methyl]-4-(4-fluorophenyl)piperidine; CAS #61869-08-7);

escitalopram (Cipralex®) ((S)-1-3-dimethylamino-propyl-1-(4'-fluoro-phenyl)-1,3-dihydro-isobenzofuran-5-carbonitril, oxalate);

femoxetine ((+)-trans-3-[(4-methoxyphenoxy)methyl]-N-methyl-4-phenyl piperidine; CAS #59859-58-4);

ifoxetine ((+/−)-cis-4-(2,3-xylyloxy)-3-piperidinol (sulfate); CAS #66208-11-5);

indeloxazine ((+/−)-2-[(1H-inden-7-yloxy)methyl]morpholine hydrochloride; CAS #60929-23-9);

binedaline (1-[[2-(dimethylamino)ethyl]methyl]amino-3-phenylindole; CAS #60662-16-0);

nefazodone (1-[3-[4-(m-chlorophenyl)-1-piperazinyl]propyl]-3-ethyl-4-(2-phenoxyethyl)-$^2$-1,2,4-triazolin-5-one (HCl); CAS #83366-66-9);

trazodone (2-[3-[4-(3-chlorophenyl)-1-piperazinyl]propyl]-1,2,4-triazolo[4,3-a]pyridin-3(2H)-one (hydrochloride); CAS #19794-93-5);

etoperidone (1-[3-[4-(m-chlorophenyl)-1-piperazinyl]propyl]-3,4-diethyl-$\Delta^2$-1,2,4-triazolin-5-one (hydrochloride); CAS #52942-31-1);

milnacipran ((+/−)-cis-2-aminomethyl-N,N-diethyl-1-phenylcyclopropane-carboxamide (hydrochloride); CAS #92623-85-3);

venlafaxine (Effexor® Wyeth) (CAS #93413-69-5);

desvenlafaxine (phenol, 4-[2-(dimethylamino)-1-(1-hydroxycyclohexyl)ethyl]-(Z)-2-butanedioate (1:1) monohydrate) (metabolite of venlafaxine); and pharmaceutically acceptable salts thereof (for example: citalopram hydrobromide CAS #59729-32-7; fluoxetine hydrochloride CAS #59333-67-4; fluvoxamine maleate CAS #61718-82-9; paroxetine hydrochloride CAS #78246-49-8; and sertraline hydrochloride 79559-97-0).

Anti-Psychotics

Anti-psychotic or neuroleptic agents are drugs that control agitated psychotic behavior, ameliorate disorders relating to thought and perception, and generally exert a calming effect. Atypical anti-psychotic or neuroleptic agents may be distinguished from "typical" anti-psychotic agents (for example, chlorpromazine or haloperidol) by their decreased extra-pyramidal side effects, especially dystonias.

Atypical anti-psychotics or atypical neuroleptics often include serotonin-2(5-HT2) and dopamine-2(D2) receptor antagonists. Examples of atypical anti-psychotics include, without limitation, 5-HT1A agonists (for example, ziprasidone: 5-[2-[4-(1,2-benzoisothiazol-3-yl)-1-piperazinyl]ethyl]-6-chloro-1,3-dihydro-2H-indol-2-one, described in U.S. Pat. Nos. 4,831,031 and 5,312,925; quetiapine: 5-[2-(4-dibenzo[b, f][1,4]thiazepin-11-yl-1-piperazinyl)ethoxy]ethanol, described in U.S. Pat. No. 4,879,288), 5-HT1A antagonists (for example, risperidone: 3-[2-[4-(6-fluoro-1,2-benzisoxazol-3-yl)piperidino]ethyl]-2-methyl-6,7,8,9-tetrahydro-4H-pyrido-[1,2-a]pyrimidin-4-one, described in U.S. Pat. No. 4,804,663; sertindole: 1-[2-[4-[5-chloro-1-(4-fluorophenyl)-1H-indol-3-yl]-1-piperidinyl]ethyl]imidazolidin-2-one, described in U.S. Pat. Nos. 4,710,500, 5,112,838, and 5,238,945), and α1-adrenoceptor antagonists (for example, clozapine: 8-chloro-11-(4-methyl-1-piperazinyl)-5H-dibenzo[b, e][1,4]diazepine, described in U.S. Pat. No. 3,539,573, and in Hanes, et al., 1988, Psychopharmacol. Bull. 24:62; olanzapine: 2-methyl-4-(4-methyl-1-piperazinyl)-1OH-thieno[2,3-b][1,5]benzodiazepine, described in U.S. Pat. No. 5,229,382). Most have an affinity for the 5-HT2 receptor (for example, zotepine: 2-[(8-chlorodibenzo[b, f]thiepin-10-yl)oxy]-N,N-dimethylethylamine, described in British Patent 1,247,067, ziprasidone, quetiapine, sertindole, risperidone, and olanzapine).

Administration of atypical anti-psychotics or neuroleptics is recommended at the lowest possible dose consistent with a therapeutic response to reduce emerging extra-pyramidal symptoms, to minimize frequency and severity of side effects and toxicity. Patients may be routinely assessed for breast tenderness or galactorrhea, as an alternative clinical monitoring technique, for evidence of increasing serum levels of atypical neuroleptics.

Anti-psychotics, for example, atypical anti-psychotics, have been used for a variety of indications, including treatment of schizophrenia, manic episodes of bipolar disorder, agitation and psychotic symptoms of dementia, Tourette's Syndrome, and other disorders that manifest psychotic or agitated symptoms.

Compositions and Administration

Subjects having or at risk for apathy, dementia, or depression may be administered a pharmaceutically effective amount of a MAOI, RIMA, or SSRI in combination with an anti-psychotic agent, for example, an atypical anti-psychotic agent, or pharmaceutically acceptable derivatives or salts thereof, formulated in a pharmaceutically acceptable carrier or diluent. A "pharmaceutically acceptable carrier" or "excipient" includes any and all solvents, dispersion media, coatings, antibacterial and antifungal agents, isotonic and absorption delaying agents, and the like that are physiologically compatible. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. In some embodiments, supplementary active compounds can also be incorporated into the compositions.

A "pharmaceutically acceptable salt" includes salts of a MAOI, RIMA, SSRI, or anti-psychotic agent derived from the combination of any of these agents and an organic or inorganic acid or base. Such agents are useful in both non-ionized and salt form. In practice, the use of a salt form amounts to use of a base form; both forms are within the scope of the invention. As used herein, the term pharmaceutically acceptable salts or complexes refers to salts or complexes that retain the desired biological activity of the above-identified compounds and exhibit minimal undesired toxicological effects. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylene-diamine, D-glucosamine, ammonium, tetraethylammonium, or ethylenediamine; or (c) combinations of (a) and (b); e.g., a zinc tannate salt or the like.

Conventional pharmaceutical practice is employed to provide suitable formulations or compositions for administration to patients. Any appropriate route of administration may be employed, for example, oral, parenteral, sublingual, intravenous, subcutaneous, intramuscular, intracranial, intraorbital, ophthalmic, intraventricular, intracapsular, intraspinal, intracisternal, intraperitoneal, intranasal, or aerosol administration. Methods well known in the art for making formulations are described, for example, in "Remington: The Science and Practice of Pharmacy" (19$^{th}$ ed.) ed. A. R. Gennaro, 1995, Mack Publishing Company, Easton, Pa., USA. The active compound(s) can also be administered through a transdermal patch (see, for example, Brown L. and Langer R.—Transdermal Delivery of Drugs, Annual Review of Medicine, 39:221-229 (1988)).

Oral formulations generally include an inert diluent or an edible carrier. For oral administration, the active compound(s) may be incorporated with excipients and used, for example, in the form of tablets, troches, or capsules or liquids. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Methods for encapsulating compositions (such as in a coating of hard gelatin) for oral administration are well known (see, for example, Baker, Richard, Controlled Release of Biological Active Agents, John Wiley and Sons, 1986).

Formulations for parenteral, intradermal, subcutaneous, or topical application may be in the form of liquid solutions or suspensions and may contain, for example, excipients, sterile water, saline, polyalkylene glycols such as polyethylene glycol, propylene glycol or other synthetic solvents, oils of vegetable origin, fixed oils, or hydrogenated napthalenes, glycerine; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of toxicity such as sodium chloride or dextrose. If administered intravenously, the carriers may be physiological saline or phosphate buffered saline (PBS). Intranasal formulations may be in the form of powders, nasal drops, or aerosols. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, slow release or extended release delivery systems may be utilized to protect the compound(s) against rapid elimination from the body. These include implants and microencapsulated delivery systems. Biocompatible, biodegradable polymers, such as ethylene vinyl acetate, polyanhydrides, polyglycolic acid, collagen, polyorthoesters, polylactic acid, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes (see, for example, U.S. Pat. No. 4,522,811).

The MAOI, RIMA, or SSRI may be administered in a separate formulation from the anti-psychotic agent, or atypical anti-psychotic agent, or may be administered in a single formulation. In some embodiments, a single formulation containing both drugs may be used to improve patient compliance. However, individual formulations of the drugs may facilitate individual dosage adjustments.

A preferred dosage range for pharmaceutically effective amounts of the compounds may be delivered to achieve peak plasma concentrations of any value between 0.1 nM-0.1M, 0.1 nM-0.05M, 0.05 nM-15 µM, or 0.01 nM-1 µM. The concentration of active compound in the drug composition will depend on absorption, distribution, inactivation, and excretion rates of the drug as well as other standard factors. Daily dosages of each of the active compound(s) may range from about 0.1 to about 5000 mg, or from about 0.5 to about 1000 mg, or 1 to 500 mg, or 10 to 100 mg. The compound may administered in any suitable unit dosage form of active ingredient. In some embodiments, the combination of the MAOI, RIMA, or SSRI and the anti-psychotic agent, or atypical anti-psychotic agent, will be at least 10%, 20%, 30%, 40%, 50%, 60%, 70%, 80%, 90%, or 100% more effective in treating apathy, dementia, or depression, than any of the compounds alone.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound in the composition may vary according to factors such as the disease-state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. Dosage unit form, as used herein, refers to physically discrete units suited as unitary dosages for subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment in individuals. In general, the compound(s) are administered in a dosage sufficient to deliver to a patient a therapeutically or prophylactically effective amount without causing serious toxic effects, although in particularly severe disorders a certain amount of toxicity or side effects may be tolerated.

The methods, uses, pharmaceutical compositions and kits described herein for the treatment of apathy, dementia, or depression may utilize or comprise a combination of one or more monoamine oxidase inhibitors in combination with one or more atypical anti-psychotic agents. Alternatively, the methods, uses, pharmaceutical compositions and kits described herein for the treatment of apathy, dementia, or depression may utilize or comprise a combination of one or more selective serotonin reuptake inhibitors in combination with one or more atypical anti-psychotic agents. Furthermore, such compositions may be in separate formulations or may be administered in a single formulation. Also, it will be appreciated that active agents described herein as monoamine oxidase inhibitors, selective serotonin reuptake inhibitors and atypical anti-psychotic agents may take the form of a metabolite or a precursor, which when metabolised forms an active agent. Representative examples of single monoamine oxidase inhibitors or single selective serotonin reuptake inhibitors in combination with an atypical anti-psychotic agent are shown in TABLE 1 below.

TABLE 1

| | monoamine oxidase inhibitor or a selective serotonin reuptake inhibitor | atypical anti-psychotic agent |
|---|---|---|
| 1. | isocarboxazid | ziprasidone |
| 2. | pargyline | ziprasidone |
| 3. | selegiline | ziprasidone |
| 4. | furazolidone | ziprasidone |
| 5. | phenelzine | ziprasidone |
| 6. | amiflamine | ziprasidone |
| 7. | iproniazid | ziprasidone |
| 8. | nialamide | ziprasidone |
| 9. | tranylcypromine | ziprasidone |
| 10. | octamoxin | ziprasidone |
| 11. | phenoxypropazine | ziprasidone |
| 12. | pivalyl benzhydrazine; | ziprasidone |
| 13. | iproclozide | ziprasidone |
| 14. | iproniazide | ziprasidone |
| 15. | bifemelane | ziprasidone |
| 16. | prodipine | ziprasidone |
| 17. | benmoxin | ziprasidone |
| 18. | etryptamine | ziprasidone |
| 19. | fenoxypropazine | ziprasidone |
| 20. | mebanazine | ziprasidone |
| 21. | pheniprazine | ziprasidone |
| 22. | safrazine | ziprasidone |
| 23. | hypericine | ziprasidone |
| 24. | iproniazid phosphate | ziprasidone |
| 25. | phenelzine sulphate | ziprasidone |
| 26. | tranylcypromine sulphate | ziprasidone |
| 27. | moclobemide | ziprasidone |
| 28. | brofaromine | ziprasidone |
| 29. | befloxatone | ziprasidone |
| 30. | toloxatone | ziprasidone |
| 31. | clorgyline | ziprasidone |
| 32. | L 51. 641 | ziprasidone |
| 33. | L 54. 761 | ziprasidone |
| 34. | L 54. 832 | ziprasidone |
| 35. | LY 121. 768 | ziprasidone |
| 36. | cimoxatone | ziprasidone |
| 37. | bazinaprine | ziprasidone |
| 38. | BW-1370U87 | ziprasidone |
| 39. | E-2011 | ziprasidone |
| 40. | harmine | ziprasidone |
| 41. | harmaline | ziprasidone |
| 42. | RS-8359 | ziprasidone |
| 43. | T-794 | ziprasidone |
| 44. | MDL 72394 | ziprasidone |
| 45. | MDL 72392 | ziprasidone |
| 46. | sercloremine | ziprasidone |
| 47. | esuprone | ziprasidone |
| 48. | clorgyline hydrochloride | ziprasidone |
| 49. | fluoxetine | ziprasidone |
| 50. | citalopram | ziprasidone |
| 51. | fluvoxamine | ziprasidone |
| 52. | sertraline | ziprasidone |
| 53. | paroxetine | ziprasidone |
| 54. | escitalopram | ziprasidone |
| 55. | femoxetine | ziprasidone |
| 56. | ifoxetine | ziprasidone |
| 57. | indeloxazine | ziprasidone |
| 58. | binedaline | ziprasidone |
| 59. | nefazodone | ziprasidone |
| 60. | trazodone | ziprasidone |
| 61. | etoperidone | ziprasidone |
| 62. | milnacipran | ziprasidone |
| 63. | venlafaxine | ziprasidone |
| 64. | desvenlafaxine | ziprasidone |
| 65. | citalopram hydrobromide | ziprasidone |
| 66. | fluoxetine hydrochloride | ziprasidone |
| 67. | fluvoxamine maleate | ziprasidone |
| 68. | paroxetine hydrochloride | ziprasidone |
| 69. | sertraline hydrochloride | ziprasidone |
| 70. | isocarboxazid | quetiapine |
| 71. | pargyline | quetiapine |
| 72. | selegiline | quetiapine |
| 73. | furazolidone | quetiapine |
| 74. | phenelzine | quetiapine |
| 75. | amiflamine | quetiapine |
| 76. | iproniazid | quetiapine |

TABLE 1-continued

| | monoamine oxidase inhibitor or a selective serotonin reuptake inhibitor | atypical anti-psychotic agent |
|---|---|---|
| 77. | nialamide | quetiapine |
| 78. | tranylcypromine | quetiapine |
| 79. | octamoxin | quetiapine |
| 80. | phenoxypropazine | quetiapine |
| 81. | pivalyl benzhydrazine; | quetiapine |
| 82. | iproclozide | quetiapine |
| 83. | iproniazide | quetiapine |
| 84. | bifemelane | quetiapine |
| 85. | prodipine | quetiapine |
| 86. | benmoxin | quetiapine |
| 87. | etryptamine | quetiapine |
| 88. | fenoxypropazine | quetiapine |
| 89. | mebanazine | quetiapine |
| 90. | pheniprazine | quetiapine |
| 91. | safrazine | quetiapine |
| 92. | hypericine | quetiapine |
| 93. | iproniazid phosphate | quetiapine |
| 94. | phenelzine sulphate | quetiapine |
| 95. | tranylcypromine sulphate | quetiapine |
| 96. | moclobemide | quetiapine |
| 97. | brofaromine | quetiapine |
| 98. | befloxatone | quetiapine |
| 99. | toloxatone | quetiapine |
| 100. | clorgyline | quetiapine |
| 101. | L 51. 641 | quetiapine |
| 102. | L 54. 761 | quetiapine |
| 103. | L 54. 832 | quetiapine |
| 104. | LY 121. 768 | quetiapine |
| 105. | cimoxatone | quetiapine |
| 106. | bazinaprine | quetiapine |
| 107. | BW-1370U87 | quetiapine |
| 108. | E-2011 | quetiapine |
| 109. | harmine | quetiapine |
| 110. | harmaline | quetiapine |
| 111. | RS-8359 | quetiapine |
| 112. | T-794 | quetiapine |
| 113. | MDL 72394 | quetiapine |
| 114. | MDL 72392 | quetiapine |
| 115. | sercloremine | quetiapine |
| 116. | esuprone | quetiapine |
| 117. | clorgyline hydrochloride | quetiapine |
| 118. | fluoxetine | quetiapine |
| 119. | citalopram | quetiapine |
| 120. | fluvoxamine | quetiapine |
| 121. | sertraline | quetiapine |
| 122. | paroxetine | quetiapine |
| 123. | escitalopram | quetiapine |
| 124. | femoxetine | quetiapine |
| 125. | ifoxetine | quetiapine |
| 126. | indeloxazine | quetiapine |
| 127. | binedaline | quetiapine |
| 128. | nefazodone | quetiapine |
| 129. | trazodone | quetiapine |
| 130. | etoperidone | quetiapine |
| 131. | milnacipran | quetiapine |
| 132. | venlafaxine | quetiapine |
| 133. | desvenlafaxine | quetiapine |
| 134. | citalopram hydrobromide | quetiapine |
| 135. | fluoxetine hydrochloride | quetiapine |
| 136. | fluvoxamine maleate | quetiapine |
| 137. | paroxetine hydrochloride | quetiapine |
| 138. | sertraline hydrochloride | quetiapine |
| 139. | isocarboxazid | risperidone |
| 140. | pargyline | risperidone |
| 141. | selegiline | risperidone |
| 142. | furazolidone | risperidone |
| 143. | phenelzine | risperidone |
| 144. | amiflamine | risperidone |
| 145. | iproniazid | risperidone |
| 146. | nialamide | risperidone |
| 147. | tranylcypromine | risperidone |
| 148. | octamoxin | risperidone |
| 149. | phenoxypropazine | risperidone |
| 150. | pivalyl benzhydrazine; | risperidone |
| 151. | iproclozide | risperidone |
| 152. | iproniazide | risperidone |
| 153. | bifemelane | risperidone |
| 154. | prodipine | risperidone |
| 155. | benmoxin | risperidone |
| 156. | etryptamine | risperidone |
| 157. | fenoxypropazine | risperidone |
| 158. | mebanazine | risperidone |
| 159. | pheniprazine | risperidone |
| 160. | safrazine | risperidone |
| 161. | hypericine | risperidone |
| 162. | iproniazid phosphate | risperidone |
| 163. | phenelzine sulphate | risperidone |
| 164. | tranylcypromine sulphate | risperidone |
| 165. | moclobemide | risperidone |
| 166. | brofaromine | risperidone |
| 167. | befloxatone | risperidone |
| 168. | toloxatone | risperidone |
| 169. | clorgyline | risperidone |
| 170. | L 51. 641 | risperidone |
| 171. | L 54. 761 | risperidone |
| 172. | L 54. 832 | risperidone |
| 173. | LY 121. 768 | risperidone |
| 174. | cimoxatone | risperidone |
| 175. | bazinaprine | risperidone |
| 176. | BW-1370U87 | risperidone |
| 177. | E-2011 | risperidone |
| 178. | harmine | risperidone |
| 179. | harmaline | risperidone |
| 180. | RS-8359 | risperidone |
| 181. | T-794 | risperidone |
| 182. | MDL 72394 | risperidone |
| 183. | MDL 72392 | risperidone |
| 184. | sercloremine | risperidone |
| 185. | esuprone | risperidone |
| 186. | clorgyline hydrochloride | risperidone |
| 187. | fluoxetine | risperidone |
| 188. | citalopram | risperidone |
| 189. | fluvoxamine | risperidone |
| 190. | sertraline | risperidone |
| 191. | paroxetine | risperidone |
| 192. | escitalopram | risperidone |
| 193. | femoxetine | risperidone |
| 194. | ifoxetine | risperidone |
| 195. | indeloxazine | risperidone |
| 196. | binedaline | risperidone |
| 197. | nefazodone | risperidone |
| 198. | trazodone | risperidone |
| 199. | etoperidone | risperidone |
| 200. | milnacipran | risperidone |
| 201. | venlafaxine | risperidone |
| 202. | desvenlafaxine | risperidone |
| 203. | citalopram hydrobromide | risperidone |
| 204. | fluoxetine hydrochloride | risperidone |
| 205. | fluvoxamine maleate | risperidone |
| 206. | paroxetine hydrochloride | risperidone |
| 207. | sertraline hydrochloride | risperidone |
| 208. | isocarboxazid | sertindole |
| 209. | pargyline | sertindole |
| 210. | selegiline | sertindole |
| 211. | furazolidone | sertindole |
| 212. | phenelzine | sertindole |
| 213. | amiflamine | sertindole |
| 214. | iproniazid | sertindole |
| 215. | nialamide | sertindole |
| 216. | tranylcypromine | sertindole |
| 217. | octamoxin | sertindole |
| 218. | phenoxypropazine | sertindole |
| 219. | pivalyl benzhydrazine; | sertindole |
| 220. | iproclozide | sertindole |
| 221. | iproniazide | sertindole |
| 222. | bifemelane | sertindole |
| 223. | prodipine | sertindole |
| 224. | benmoxin | sertindole |
| 225. | etryptamine | sertindole |
| 226. | fenoxypropazine | sertindole |
| 227. | mebanazine | sertindole |
| 228. | pheniprazine | sertindole |

TABLE 1-continued

| | monoamine oxidase inhibitor or a selective serotonin reuptake inhibitor | atypical anti-psychotic agent |
|---|---|---|
| 229. | safrazine | sertindole |
| 230. | hypericine | sertindole |
| 231. | iproniazid phosphate | sertindole |
| 232. | phenelzine sulphate | sertindole |
| 233. | tranylcypromine sulphate | sertindole |
| 234. | moclobemide | sertindole |
| 235. | brofaromine | sertindole |
| 236. | befloxatone | sertindole |
| 237. | toloxatone | sertindole |
| 238. | clorgyline | sertindole |
| 239. | L 51. 641 | sertindole |
| 240. | L 54. 761 | sertindole |
| 241. | L 54. 832 | sertindole |
| 242. | LY 121. 768 | sertindole |
| 243. | cimoxatone | sertindole |
| 244. | bazinaprine | sertindole |
| 245. | BW-1370U87 | sertindole |
| 246. | E-2011 | sertindole |
| 247. | harmine | sertindole |
| 248. | harmaline | sertindole |
| 249. | RS-8359 | sertindole |
| 250. | T-794 | sertindole |
| 251. | MDL 72394 | sertindole |
| 252. | MDL 72392 | sertindole |
| 253. | sercloremine | sertindole |
| 254. | esuprone | sertindole |
| 255. | clorgyline hydrochloride | sertindole |
| 256. | fluoxetine | sertindole |
| 257. | citalopram | sertindole |
| 258. | fluvoxamine | sertindole |
| 259. | sertraline | sertindole |
| 260. | paroxetine | sertindole |
| 261. | escitalopram | sertindole |
| 262. | femoxetine | sertindole |
| 263. | ifoxetine | sertindole |
| 264. | indeloxazine | sertindole |
| 265. | binedaline | sertindole |
| 266. | nefazodone | sertindole |
| 267. | trazodone | sertindole |
| 268. | etoperidone | sertindole |
| 269. | milnacipran | sertindole |
| 270. | venlafaxine | sertindole |
| 271. | desvenlafaxine | sertindole |
| 272. | citalopram hydrobromide | sertindole |
| 273. | fluoxetine hydrochloride | sertindole |
| 274. | fluvoxamine maleate | sertindole |
| 275. | paroxetine hydrochloride | sertindole |
| 276. | sertraline hydrochloride | sertindole |
| 277. | isocarboxazid | clozapine |
| 278. | pargyline | clozapine |
| 279. | selegiline | clozapine |
| 280. | furazolidone | clozapine |
| 281. | phenelzine | clozapine |
| 282. | amiflamine | clozapine |
| 283. | iproniazid | clozapine |
| 284. | nialamide | clozapine |
| 285. | tranylcypromine | clozapine |
| 286. | octamoxin | clozapine |
| 287. | phenoxypropazine | clozapine |
| 288. | pivalyl benzhydrazine; | clozapine |
| 289. | iproclozide | clozapine |
| 290. | iproniazide | clozapine |
| 291. | bifemelane | clozapine |
| 292. | prodipine | clozapine |
| 293. | benmoxin | clozapine |
| 294. | etryptamine | clozapine |
| 295. | fenoxypropazine | clozapine |
| 296. | mebanazine | clozapine |
| 297. | pheniprazine | clozapine |
| 298. | safrazine | clozapine |
| 299. | hypericine | clozapine |
| 300. | iproniazid phosphate | clozapine |
| 301. | phenelzine sulphate | clozapine |
| 302. | tranylcypromine sulphate | clozapine |
| 303. | moclobemide | clozapine |
| 304. | brofaromine | clozapine |
| 305. | befloxatone | clozapine |
| 306. | toloxatone | clozapine |
| 307. | clorgyline | clozapine |
| 308. | L 51. 641 | clozapine |
| 309. | L 54. 761 | clozapine |
| 310. | L 54. 832 | clozapine |
| 311. | LY 121. 768 | clozapine |
| 312. | cimoxatone | clozapine |
| 313. | bazinaprine | clozapine |
| 314. | BW-1370U87 | clozapine |
| 315. | E-2011 | clozapine |
| 316. | harmine | clozapine |
| 317. | harmaline | clozapine |
| 318. | RS-8359 | clozapine |
| 319. | T-794 | clozapine |
| 320. | MDL 72394 | clozapine |
| 321. | MDL 72392 | clozapine |
| 322. | sercloremine | clozapine |
| 323. | esuprone | clozapine |
| 324. | clorgyline hydrochloride | clozapine |
| 325. | fluoxetine | clozapine |
| 326. | citalopram | clozapine |
| 327. | fluvoxamine | clozapine |
| 328. | sertraline | clozapine |
| 329. | paroxetine | clozapine |
| 330. | escitalopram | clozapine |
| 331. | femoxetine | clozapine |
| 332. | ifoxetine | clozapine |
| 333. | indeloxazine | clozapine |
| 334. | binedaline | clozapine |
| 335. | nefazodone | clozapine |
| 336. | trazodone | clozapine |
| 337. | etoperidone | clozapine |
| 338. | milnacipran | clozapine |
| 339. | venlafaxine | clozapine |
| 340. | desvenlafaxine | clozapine |
| 341. | citalopram hydrobromide | clozapine |
| 342. | fluoxetine hydrochloride | clozapine |
| 343. | fluvoxamine maleate | clozapine |
| 344. | paroxetine hydrochloride | clozapine |
| 345. | sertraline hydrochloride | clozapine |
| 346. | isocarboxazid | zotepine |
| 347. | pargyline | zotepine |
| 348. | selegiline | zotepine |
| 349. | furazolidone | zotepine |
| 350. | phenelzine | zotepine |
| 351. | amiflamine | zotepine |
| 352. | iproniazid | zotepine |
| 353. | nialamide | zotepine |
| 354. | tranylcypromine | zotepine |
| 355. | octamoxin | zotepine |
| 356. | phenoxypropazine | zotepine |
| 357. | pivalyl benzhydrazine; | zotepine |
| 358. | iproclozide | zotepine |
| 359. | iproniazide | zotepine |
| 360. | bifemelane | zotepine |
| 361. | prodipine | zotepine |
| 362. | benmoxin | zotepine |
| 363. | etryptamine | zotepine |
| 364. | fenoxypropazine | zotepine |
| 365. | mebanazine | zotepine |
| 366. | pheniprazine | zotepine |
| 367. | safrazine | zotepine |
| 368. | hypericine | zotepine |
| 369. | iproniazid phosphate | zotepine |
| 370. | phenelzine sulphate | zotepine |
| 371. | tranylcypromine sulphate | zotepine |
| 372. | moclobemide | zotepine |
| 373. | brofaromine | zotepine |
| 374. | befloxatone | zotepine |
| 375. | toloxatone | zotepine |
| 376. | clorgyline | zotepine |
| 377. | L 51. 641 | zotepine |
| 378. | L 54. 761 | zotepine |
| 379. | L 54. 832 | zotepine |
| 380. | LY 121. 768 | zotepine |

TABLE 1-continued

| | monoamine oxidase inhibitor or a selective serotonin reuptake inhibitor | atypical anti-psychotic agent |
|---|---|---|
| 381. | cimoxatone | zotepine |
| 382. | bazinaprine | zotepine |
| 383. | BW-1370U87 | zotepine |
| 384. | E-2011 | zotepine |
| 385. | harmine | zotepine |
| 386. | harmaline | zotepine |
| 387. | RS-8359 | zotepine |
| 388. | T-794 | zotepine |
| 389. | MDL 72394 | zotepine |
| 390. | MDL 72392 | zotepine |
| 391. | sercloremine | zotepine |
| 392. | esuprone | zotepine |
| 393. | clorgyline hydrochloride | zotepine |
| 394. | fluoxetine | zotepine |
| 395. | citalopram | zotepine |
| 396. | fluvoxamine | zotepine |
| 397. | sertraline | zotepine |
| 398. | paroxetine | zotepine |
| 399. | escitalopram | zotepine |
| 400. | femoxetine | zotepine |
| 401. | ifoxetine | zotepine |
| 402. | indeloxazine | zotepine |
| 403. | binedaline | zotepine |
| 404. | nefazodone | zotepine |
| 405. | trazodone | zotepine |
| 406. | etoperidone | zotepine |
| 407. | milnacipran | zotepine |
| 408. | venlafaxine | zotepine |
| 409. | desvenlafaxine | zotepine |
| 410. | citalopram hydrobromide | zotepine |
| 411. | fluoxetine hydrochloride | zotepine |
| 412. | fluvoxamine maleate | zotepine |
| 413. | paroxetine hydrochloride | zotepine |
| 414. | sertraline hydrochloride | zotepine |
| 415. | isocarboxazid | olanzapine |
| 416. | pargyline | olanzapine |
| 417. | selegiline | olanzapine |
| 418. | furazolidone | olanzapine |
| 419. | phenelzine | olanzapine |
| 420. | amiflamine | olanzapine |
| 421. | iproniazid | olanzapine |
| 422. | nialamide | olanzapine |
| 423. | tranylcypromine | olanzapine |
| 424. | octamoxin | olanzapine |
| 425. | phenoxypropazine | olanzapine |
| 426. | pivalyl benzhydrazine; | olanzapine |
| 427. | iproclozide | olanzapine |
| 428. | iproniazide | olanzapine |
| 429. | bifemelane | olanzapine |
| 430. | prodipine | olanzapine |
| 431. | benmoxin | olanzapine |
| 432. | etryptamine | olanzapine |
| 433. | fenoxypropazine | olanzapine |
| 434. | mebanazine | olanzapine |
| 435. | pheniprazine | olanzapine |
| 436. | safrazine | olanzapine |
| 437. | hypericine | olanzapine |
| 438. | iproniazid phosphate | olanzapine |
| 439. | phenelzine sulphate | olanzapine |
| 440. | tranylcypromine sulphate | olanzapine |
| 441. | moclobemide | olanzapine |
| 442. | brofaromine | olanzapine |
| 443. | befloxatone | olanzapine |
| 444. | toloxatone | olanzapine |
| 445. | clorgyline | olanzapine |
| 446. | L 51. 641 | olanzapine |
| 447. | L 54. 761 | olanzapine |
| 448. | L 54. 832 | olanzapine |
| 449. | LY 121. 768 | olanzapine |
| 450. | cimoxatone | olanzapine |
| 451. | bazinaprine | olanzapine |
| 452. | BW-1370U87 | olanzapine |
| 453. | E-2011 | olanzapine |
| 454. | harmine | olanzapine |
| 455. | harmaline | olanzapine |
| 456. | RS-8359 | olanzapine |
| 457. | T-794 | olanzapine |
| 458. | MDL 72394 | olanzapine |
| 459. | MDL 72392 | olanzapine |
| 460. | sercloremine | olanzapine |
| 461. | esuprone | olanzapine |
| 462. | clorgyline hydrochloride | olanzapine |
| 463. | fluoxetine | olanzapine |
| 464. | citalopram | olanzapine |
| 465. | fluvoxamine | olanzapine |
| 466. | sertraline | olanzapine |
| 467. | paroxetine | olanzapine |
| 468. | escitalopram | olanzapine |
| 469. | femoxetine | olanzapine |
| 470. | ifoxetine | olanzapine |
| 471. | indeloxazine | olanzapine |
| 472. | binedaline | olanzapine |
| 473. | nefazodone | olanzapine |
| 474. | trazodone | olanzapine |
| 475. | etoperidone | olanzapine |
| 476. | milnacipran | olanzapine |
| 477. | venlafaxine | olanzapine |
| 478. | desvenlafaxine | olanzapine |
| 479. | citalopram hydrobromide | olanzapine |
| 480. | fluoxetine hydrochloride | olanzapine |
| 481. | fluvoxamine maleate | olanzapine |
| 482. | paroxetine hydrochloride | olanzapine |
| 483. | sertraline hydrochloride | olanzapine |

Example 1A

A pharmaceutical composition is prepared by combining moclobemide with any one of risperidone, olanzapine, zotepine, ziprasidone, quetiapine, sertindole, or clozapine in a pharmaceutically acceptable carrier. The composition includes moclobemide at a daily dosage of about 75 mg to about 600 mg, and any one of risperidone at a daily dosage of about 0.25 mg to about 3 mg, olanzapine at a daily dosage of about 0.625 mg to about 10 mg, zotepine at a daily dosage of about 12.5 mg to about 300 mg, ziprasidone at a daily dosage of about 1.00 mg to about 80 mg, quetiapine at a daily dosage of about 12.5 mg to about 800 mg, sertindole at a daily dosage of about 6.25 mg to about 450 mg or clozapine at a daily dosage of about 1.00 mg to about 900 mg, per day, respectively. The composition is administered to a patient for treating dementia, depression, or apathy.

Example 1B

A pharmaceutical composition is prepared by combining moclobemide with any one of risperidone, olanzapine, zotepine, ziprasidone, quetiapine, sertindole, or clozapine in a pharmaceutically acceptable carrier. The composition includes moclobemide at a daily dosage of about 150 mg to about 600 mg, and any one of risperidone at a daily dosage of about 0.625 mg to about 3 mg, olanzapine at a daily dosage of about 0.625 mg to about 10 mg, zotepine at a daily dosage of about 12.5 mg to about 300 mg, ziprasidone at a daily dosage of about 1.00 mg to about 80 mg, quetiapine at a daily dosage of about 12.5 mg to about 800 mg, sertindole at a daily dosage of about 6.25 mg to about 450 mg or clozapine at a daily dosage of about 1.00 mg to about 900 mg, per day, respectively. The composition is administered to a patient for treating dementia, depression, or apathy.

Example 2A

A pharmaceutical composition is prepared by combining venlafaxine with any one of risperidone, olanzapine, zotepine, ziprasidone, quetiapine, sertindole, or clozapine in a pharmaceutically acceptable carrier. The composition includes venlafaxine at a daily dosage of about 37.5 mg to about 375 mg, and any one of risperidone at a daily dosage of about 0.25 mg to about 3 mg, olanzapine at a daily dosage of about 0.625 mg to about 10 mg, zotepine at a daily dosage of about 12.5 mg to about 300 mg, ziprasidone at a daily dosage of about 1.00 mg to about 80 mg, quetiapine at a daily dosage of about 12.5 mg to about 800 mg, sertindole at a daily dosage of about 6.25 mg to about 450 mg or clozapine at a daily dosage of about 1.00 mg to about 900 mg, per day, respectively. The composition is administered to a patient for treating dementia, depression, or apathy. Alternatively, the composition is prepared with risperidone at a daily dosage of about 0.625 mg to about 3 mg.

Example 2B

A pharmaceutical composition is prepared by combining venlafaxine with any one of risperidone, olanzapine, zotepine, ziprasidone, quetiapine, sertindole, or clozapine in a pharmaceutically acceptable carrier. The composition includes venlafaxine at a daily dosage of about 37.5 mg to about 375 mg, and any one of risperidone at a daily dosage of about 0.625 mg to about 3 mg, olanzapine at a daily dosage of about 0.625 mg to about 10 mg, zotepine at a daily dosage of about 12.5 mg to about 300 mg, ziprasidone at a daily dosage of about 1.00 mg to about 80 mg, quetiapine at a daily dosage of about 12.5 mg to about 800 mg, sertindole at a daily dosage of about 6.25 mg to about 450 mg or clozapine at a daily dosage of about 1.00 mg to about 900 mg, per day, respectively. The composition is administered to a patient for treating dementia, depression, or apathy.

Example 3

A 44 year female Caucasian presented in referral for apathy. This individual gave 5 year history of behavioral change followed by occupational impairment, social withdrawal then frankly decreased complex attention. A diagnosis of frontotemporal dementia was made.

A treatment plan for apathy was made whereby low dose moclobemide was titrated against low dose risperidone, commenced approximately 6 months following the initial diagnosis. Subsequently (approximately 2 months later), improvement was independently documented.

A further independent evaluation was made approximately 1 year and 1 month after treatment began and improvement in her apathy was noted.

Approximately 5 months later risperidone was discontinued for pharmacokinetic limitations and olanzapine commenced. With changes in the dose of olanzapine, the apathy was again effectively treated. The patient continued her work developing an advocacy network for persons with dementia and traveling internationally. This precipitated an independent medical evaluation by her disability insurer, which substantiated her diagnosis and the treatment effect.

The combination therapy (moclobemide and risperidone or olanzapine) exhibited a clinical efficacy that appeared to be greater than the cumulative effect that would have been expected if the patient had been treated with an equivalent amount of moclobemide alone or with an equivalent amount of risperidone or olanzapine alone.

Example 4

A 49 year female was diagnosed at a specialized clinic with early onset Alzheimer's disease in 2001. Donepezil 10 mg daily was commenced. The clinical picture was complicated by a degree of anxiety and depressed mood. The depressed mood responded to venlafaxine 150 mg daily. The anxiety improved by systematically addressing life course issues.

Independent reassessment in 2003 by the specialized clinic revealed a mild degree of further cognitive decline with good compensating skills compensating well for some deficits. Venlafaxine was tapered and discontinued for excessive sweating. Moclobemide was commenced in place of venlafaxine. Risperidone was eventually prescribed at 0.25 mg daily. Her performance in Instrumental Activities of Daily Living (IADL's) improved as did the breadth and sophistication of her social activities.

Subsequent independent re-assessment by a specialized clinic in 2004 revealed cognitive improvement compared with the 2003 assessment and improvement on some test items on the original 2001 diagnostic assessment.

The emergence of dystonia with risperidone was managed by discontinuing the risperidone and commencing quetiapine. The overall improvement in IADL's and social function continued.

Example 5

A 79 year old retired sailor developed Parkinson's disease more than 5 years before admission to hospital. After the onset of Parkinson's disease he developed decreased motivation and decreased interest. The severity of the apathy progressed to a near total lack of initiative. A trial of methylphenidate for apathy was unsuccessful. He was admitted to hospital with anxiety, severe apathy and constipation. He was unable to function at home leading to caregiver burn out.

Core symptoms of delirium were absent. A shuffling gait devoid of heel strike or toe push was observed. Arm swing was decreased. This gentleman described decreased motivation in face of clear enjoyment of family visits and the sunshine outside. His capacity for projective pleasure was preserved. He was satisfied with his accomplishments over his life. He felt his quality of life was reduced by his lack initiative. Objective mood and affect were flat. Thought form was marked by latency but progressed logically to a goal oriented conclusion. Thought content was free of delusions or hallucinations. Language was mildly impaired with paraphasic errors noted. Remote memories were difficult to recall and approximately correct. His sense of humor and capacity for abstraction were preserved.

Wechsler Adult Intelligence Scale®—Third Edition (WAIS III) testing revealed mild impairment of attention, praxis, reasoning, memory, response latency and difficulty in self correcting. This was judged consistent with Parkinson's disease by the registered psychologist.

An occupational therapy assessment in hospital on day 2 revealed decreased grip strength compromising his ability to dress and decreased range of movement compromising bathing. He could walk four lengths of the hallway.

Moclobemide was commenced day 4 at 75 mg. daily, increased to 150 mg. daily on day 8 and decreased to 75 mg daily on day 11. Olanzapine was commenced day 8 at 1.25 mg daily and continued at that dose.

Day 8 to 11 demonstrated the absence of depression by every day life. He enjoyed watching the Superbowl. He came into a small financial windfall and developed several plans to spend the money. Increased energy and increased social interaction were observed. Increased spontaneous activity led to independence in Activities of Daily Living (ADL). His walking improved to 400 feet.

Day 15 to 17 revealed increased mobile facial expression. He was able to learn, retain and employ movement strategies to eliminate postural hypotension. He was fully independent with his morning routine prior to discharge. He was discharged home independent in ADL.

Example 6

A 75 year retired nurse lived independently in the community until 2 months prior to admission. A progressive and gradual reduction in social patterns was reported over the preceding two years. However, she traveled internationally during that time.

Over the two months prior to admission she became more forgetful, refused support services, further withdrew from the community and described herself as "depressed". She acquired a thrush infection, became dehydrated and lost a great deal of weight.

Family and personal psychiatric history was negative. Salient medical history included a remote mastectomy for breast cancer, three vessel coronary bypass, acid peptic disease and hypertension.

Admitting mental status examination revealed a cachexic female suffering anxiety and lacking pleasure in previously pleasurable activities. Initiative was absent. Objective mood was dysphoric and affect restricted. Decreased concentration was apparent. The MMSE was 28/28 in nonstandard administration. She was completely dependent for activities of daily living (ADL).

Moclobemide was commenced at 200 mg. daily on day 4, increased to 300 mg. daily and day 6 and continued at 300 mg. daily.

Risperidone was commenced at 0.5 mg daily on day 7, discontinued on day 14 then restarted at 0.5 mg daily alternating with 0.25 mg. daily and continued as such.

The first three days of the admission showed prominent depressed mood in the morning with very limited improvement in the late afternoon. The late afternoon quality of mood and mobility of affect improved by Day 6.

By Day 13 pleasure was experienced and her affect mobilized. She described herself as unable to cook, clean for care for herself prior to admission. With step by step instructions she could progress through her Activities of Daily Living (ADL). Shortly after, mild extrapyramidal symptoms emerged. Therefore, risperidone was decreased.

Self-toileting emerged on Day 16. By Day 20 she reported an euthymic mood and denied treatment emergent side effects. Examination showed some mobility of affect and normal muscle tone. However, she remained without initiative to commence and complete almost all ADL.

By Day 24 self initiation of ADL was consistently observed. From Day 28 forward both self initiation and self supervision of ADL to completion was consistently observed. She resumed her usual hobby of reading on Day 45. Her 3MS score on Day 45 was 80/100. She was discharged to an intermediate care facility where she continued regular activity. Eventually she took up square dancing and returned to international travel.

Other Embodiments

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. The invention includes all embodiments and variations substantially as described herein.

What is claimed is:

1. A method of treating apathy syndrome in a human subject in need thereof, comprising administering a pharmaceutically effective amount of a monoamine oxidase inhibitor in combination with an anti-psychotic agent selected from the group consisting risperidone, olanzapine, zotepine, ziprasidone, quetiapine, sertindole, clozapine, mixtures thereof, and pharmaceutically acceptable salts thereof to the subject, wherein the subject is a subject that has been diagnosed as having apathy syndrome according to at least one of the Apathy Evaluation Scale or the Apathy Inventory, and wherein the human subject does not have abulia, akinesia, akinetic mutism, depression, dementia, delirium, despair and demoralization.

2. The method according to claim 1, wherein the monoamine oxidase inhibitor is a reversible monoamine oxidase inhibitor.

3. The method according to claim 1, wherein the reversible monoamine oxidase inhibitor is a reversible monoamine oxidase-A inhibitor.

4. The method of claim 1, wherein the reversible monoamine oxidase inhibitor is selected from the group consisting of moclobemide, brofaromine, befloxatone, toloxatone, mixtures thereof, and pharmaceutically acceptable salts thereof.

5. The method according to claim 1, wherein the monoamine oxidase inhibitor is selected from the group consisting of:
  isocarboxazid; pargyline; selegiline; furazolidone; phenelzine; amiflamine; iproniazid; nialamide; tranylcypromine; octamoxin; phenoxypropazine; pivalyl benzhydrazine; iproclozide; iproniazide; bifemelane; prodipine; benmoxin; etryptamine; fenoxypropazine; mebanazine; pheniprazine; safrazine; hypericine; iproniazid phosphate; phenelzine sulphate; tranylcypromine sulphate; moclobemide; brofaromine; befloxatone; toloxatone; clorgyline; L 51. 641; L 54. 761; L 54. 832; LY 121. 768; cimoxatone; bazinaprine; BW-1370U87; E-2011; harmine; harmaline; RS-8359; T-794; MDL 72394; MDL 72392; sercloremine; esuprone; clorgyline hydrochloride; mixtures thereof; and pharmaceutically acceptable salts thereof.

6. The method according to claim 1, wherein the combination is synergistically effective.

7. The method according to claim 1, wherein the method further comprises diagnosing the human subject as having apathy.

8. A method of treating apathy syndrome in a human subject that has been diagnosed as having apathy, comprising administering a pharmaceutically effective amount of a monoamine oxidase inhibitor in combination with an 5HT-2 receptor antagonist to the subject, wherein said 5HT-2 receptor antagonist is selected from the group consisting of zotepine, ziprasidone, quetiapine sertindole, mixtures thereof and pharmaceutically acceptable salts thereof and wherein the subject is a subject that has been diagnosed as having apathy syndrome according to at least one of the Apathy Evaluation Scale or the Apathy Inventory, and wherein the human subject does not have abulia, akinesia, akinetic mutism, depression, dementia, delirium, despair and demoralization.

9. The method according to claim 8, wherein the monoamine oxidase inhibitor is a reversible monoamine oxidase inhibitor.

10. The method according to claim 9, wherein the reversible monoamine oxidase inhibitor is a reversible monoamine oxidase-A inhibitor.

11. The method according to claim 9, wherein the reversible monoamine oxidase inhibitor is selected from the group consisting of moclobemide, brofaromine, befloxatone, toloxatone, mixtures thereof and pharmaceutically acceptable salts thereof.

12. The method according to claim 8, wherein the monoamine oxidase inhibitor is selected from the group consisting of:

isocarboxazid; pargyline; selegiline; furazolidone; phenelzine; amiflamine; iproniazid; nialamide; tranylcypromine; octamoxin; phenoxypropazine; pivalyl benzhydrazine; iproclozide; iproniazide; bifemelane; prodipine; benmoxin; etryptamine; fenoxypropazine; mebanazine; pheniprazine; safrazine; hypericine; iproniazid phosphate; phenelzine sulphate; tranylcypromine sulphate; moclobemide; brofaromine; befloxatone; toloxatone; clorgyline; L 51. 641; L 54. 761; L 54. 832; LY 121. 768; cimoxatone; bazinaprine; BW-1370U87; E-2011; harmine; harmaline; RS-8359; T-794; MDL 72394; MDL 72392; sercloremine; esuprone; clorgyline hydrochloride; mixtures thereof; and pharmaceutically acceptable salts thereof.

13. The method according to claim 4, wherein the reversible monoamine oxidase inhibitor is moclobemide.

14. The method according to claim 1, wherein the atypical anti-psychotic is selected from the group consisting of risperidone, zotepine, ziprasidone, quetiapine, sertindole, clozapine, mixtures thereof, and pharmaceutically acceptable salts thereof.

15. The method according to claim 11, wherein the reversible monoamine oxidase inhibitor is moclobemide.

* * * * *